(12) United States Patent
Jeong et al.

(10) Patent No.: US 10,809,206 B2
(45) Date of Patent: Oct. 20, 2020

(54) FLOATING-TYPE CONTAMINANT MEASURING APPARATUS

(71) Applicant: REPUBLIC OF KOREA (NATIONAL DISASTER MANAGEMENT RESEARCH INSTITUTE), Ulsan (KR)

(72) Inventors: Gun Sik Jeong, Ulsan (KR); Hyunju Kim, Ulsan (KR); KyungSu Lee, Ulsan (KR); Tae Wook Lee, Ulsan (KR); Jae Jeong Kim, Ulsan (KR)

(73) Assignee: NATIONAL DISASTER MANAGEMENT RESEARCH INSTITUTE, Ulsan (KR)

( * ) Notice: Subject to any disclaimer, the term of this patent is extended or adjusted under 35 U.S.C. 154(b) by 0 days.

(21) Appl. No.: 16/349,311

(22) PCT Filed: Nov. 29, 2017

(86) PCT No.: PCT/KR2017/013774
§ 371 (c)(1),
(2) Date: May 13, 2019

(87) PCT Pub. No.: WO2018/101726
PCT Pub. Date: Jun. 7, 2018

(65) Prior Publication Data
US 2020/0191725 A1 Jun. 18, 2020

(30) Foreign Application Priority Data
Nov. 30, 2016 (KR) .................. 10-2016-0161015

(51) Int. Cl.
*G01N 21/94* (2006.01)
*H04W 4/70* (2018.01)
(Continued)

(52) U.S. Cl.
CPC ............... *G01N 21/94* (2013.01); *G01N 1/24* (2013.01); *G08B 21/14* (2013.01); *H04W 4/70* (2018.02)

(58) Field of Classification Search
CPC ..... G01N 21/94; G01N 1/24; G01N 2001/245; G01N 2001/247; G08B 21/14; H04W 4/70
See application file for complete search history.

(56) References Cited

U.S. PATENT DOCUMENTS

| 5,481,904 A * | 1/1996 | Fleck, Sr. ............. G01N 1/12 340/605 |
| 7,690,247 B1 * | 4/2010 | Lapota ................. G01C 13/00 73/170.29 |
| 2015/0346726 A1 * | 12/2015 | Davoodi ............... B63B 22/02 701/21 |

FOREIGN PATENT DOCUMENTS

| JP | 2008176457 A | 7/2008 |
| KR | 1020110053826 A | 5/2011 |

(Continued)

OTHER PUBLICATIONS

International search report of PCT/KR2017/013774, dated Mar. 7, 2018, English translation.

*Primary Examiner* — Dennis White
(74) *Attorney, Agent, or Firm* — STIP Law Group, LLC

(57) ABSTRACT

The floating-type contamination measurement apparatus according to embodiments of the present invention can provide a body part; a buoyancy providing part, which is received to the body part and provides buoyancy to the body part; and a measurement part, which is received to the body part and measures the level of contamination in a closed space.

11 Claims, 4 Drawing Sheets

(51) Int. Cl.
*G01N 1/24* (2006.01)
*G08B 21/14* (2006.01)

(56) References Cited

FOREIGN PATENT DOCUMENTS

| KR | 1020110100361 A | 9/2011 |
| KR | 1020140105637 A | 9/2014 |
| KR | 101444451 B1 | 10/2014 |
| KR | 101662950 B1 | 10/2016 |

* cited by examiner

10

FLOATING-TYPE CONTAMINANT MEASURING APPARATUS

CROSS-REFERENCE TO RELATED APPLICATIONS

This application is the U.S. National Phase under 35 U.S.C. § 371 of International Application No. PCT/KR2017/013774 filed on Nov. 29, 2017, which in turn claims the benefit of Korean Application No. KR 10-2016-0161015, filed on Nov. 30, 2016, the disclosures of which are incorporated by reference into the present application.

FIELD OF THE INVENTION

The present invention relates to a contamination measuring device, and specifically a floating-type contamination measurement apparatus that can measure the level of contamination in a closed space.

RELATED ART

A closed space refers to a place where workers can perform work with insufficient ventilation, such as wells, vertical shafts, tunnels, caissons, culverts, manholes, tanks, reactors, septic tanks, settling tanks, sump tanks, etc.

In a case where a worker performs the work in such a confined space, the oxygen cannot be normally supplied to the worker's body and the accident may occur due to suffocation. In particular, occasionally when a worker enters a place that lacks oxygen, he/she may collapse and die in less than a few minutes without being aware of the risk of suffocation.

Additionally, in a closed space where ventilation is not sufficient, there may be harmful gases which cause a smothering action due to the poisoning of the body in addition to oxygen deficiency. Since these harmful gases cause a smothering action when the body is exposed to these harmful gases even when the oxygen concentration is in a state of normal concentration, it is necessary to confirm not only the oxygen concentration but also the concentrations of possible harmful gases in a place where there is a risk of generation of these gases.

In this regard, KR Patent Application Publication No. 10-2011-0053826 discloses a complex network system and method for safe monitoring of the harmful workshop. However, the harmful reduction sensing device in prior art employs a method where the device is fixedly attached to a harmful workplace, and thus there is a limitation in that the device cannot perform its function due to malfunction or failure of the device by the submerging of the device depending on the level of the closed space in the closed space in which a liquid material is present (e.g., a septic tank).

SUMMARY OF THE INVENTION

In an embodiment, the present invention can provide a floating-type contamination measurement apparatus which is able to measure the concentration of contamination on the water surface irrespective of the level of the liquids in a closed space.

Additionally, in another embodiment, the present invention can provide a floating-type contamination measurement apparatus which is able to prevent safety accidents by detecting the presence of harmful gases and oxygen deficiency in a closed space.

Additionally, in still another embodiment, the present invention can provide a floating-type contamination measurement apparatus which is able to check the level of danger according to the working position of a worker by providing the concentrations of harmful gases according to the height in a closed space.

Additionally, in still another embodiment, the present invention can provide a floating-type contamination measurement apparatus which is able to provide danger in an audio and visual manner in a closed space.

Additionally, in still another embodiment, the present invention can provide a floating-type contamination measurement apparatus which is able to detect the level of contamination in a state in which foreign substances are not introduced in a closed space.

The present invention according to an embodiment can provide a floating-type contamination measurement apparatus, which includes: a body part; a buoyancy providing part, which is received to the body part and provides buoyancy to the body part; and a measurement part, which is received to the body part and measures the level of contamination in a closed space.

Additionally, the present invention according to another embodiment can provide a floating-type contamination measurement apparatus, in which the measurement part detects a harmful gas in a closed space.

Additionally, the present invention according to still another embodiment can provide a floating-type contamination measurement apparatus, in which the measurement part detects the oxygen concentration in a closed space.

Additionally, the present invention according to still another embodiment can provide a floating-type contamination measurement apparatus, in which the body part comprises a suction device that sucks the gas in a closed space and a discharge device that discharges the sucked gas, and the measurement part measures the level of contamination in the closed space using the sucked gas.

Additionally, the present invention according to still another embodiment can provide a floating-type contamination measurement apparatus, in which the device further includes an operation part which operates the opening/closing of the suction device and the discharge device.

Additionally, the present invention according to still another embodiment can provide a floating-type contamination measurement apparatus, in which the buoyancy providing part further includes a weight located at a lower end region of the body part.

Additionally, the present invention according to still another embodiment can provide a floating-type contamination measurement apparatus, in which the measurement part includes a contamination measuring sensor and a processor, in which the processor measures the kinds and concentrations of harmful gases and oxygen concentration in a closed space based on the detection results from the contamination measuring sensor.

Additionally, the present invention according to still another embodiment can provide a floating-type contamination measurement apparatus, in which the measurement part further includes a position sensor that detects the position of the body part.

Additionally, the present invention according to still another embodiment can provide a floating-type contamination measurement apparatus, in which the processor detect the level of contamination in a closed space based on the detection results from the position sensor.

Additionally, the present invention according to still another embodiment can provide a floating-type contamination measurement apparatus, in which the measurement part further includes a communication part, and the processor transmits the measurement results to a monitoring device located outside of the closed space via the communication part.

Additionally, the present invention according to still another embodiment can provide a floating-type contamination measurement apparatus, in which the device further includes an alarm unit that performs the display of light emission and/or a sound based on the detection results of the measurement part.

DESCRIPTION OF EXEMPLARY EMBODIMENTS

Figure 1:
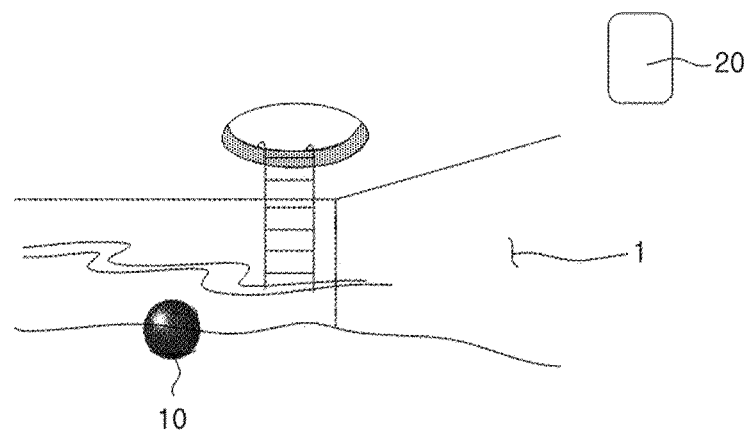
FIG. 1 is a diagram illustrating a floating-type contamination measurement apparatus and an external monitoring device located on a closed space according to an embodiment of the present invention.

Since various modifications can be made to the invention and various embodiments thereof are available, specific embodiments will be illustrated in the drawings and described in detail in the detailed description. The effects and features of the present invention and methods of achieving them will be apparent with reference to the embodiments described in detail below with reference to the drawings. However, the present invention is not limited to the embodiments disclosed hereinbelow, but it may be implemented in various forms. In the embodiments below, the terms such as first, second, etc. are used for the purpose of distinguishing one element from another element. Additionally, the singular expression may include a plural expression unless the context clearly specifies otherwise. Additionally, the terms such as comprising or having means that a feature or element described in the specification is present, and it does not exclude the possibility that one or more other features or components may be added. Additionally, in the drawings, components may be exaggerated or reduced in size for convenience of explanation. For example, the size and thickness of each component shown in the drawings are arbitrarily shown for convenience of explanation, and thus the present invention is not necessarily limited to those illustrated.

Hereinafter, exemplary embodiments of the present invention will be described in detail with reference to the accompanying drawings, in which in describing the drawings, the same or corresponding components are denoted by the same reference numerals throughout the drawings and a duplicate description thereof will be omitted.

Figure 2:
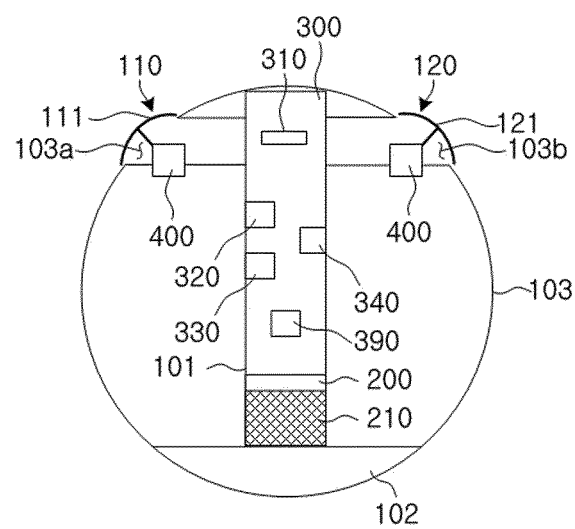
FIG. 2 is a diagram illustrating the internal configuration of a floating-type contamination measurement apparatus.
Figure 3:
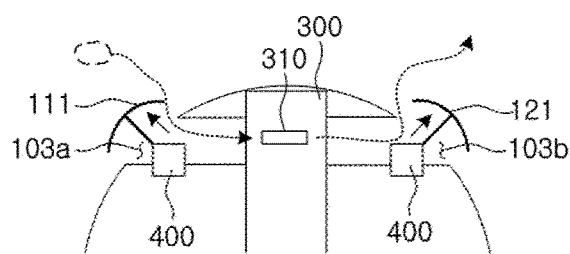
FIG. 3 is a diagram illustrating a state in which a suction device and a discharge device are opened.
Figure 4:
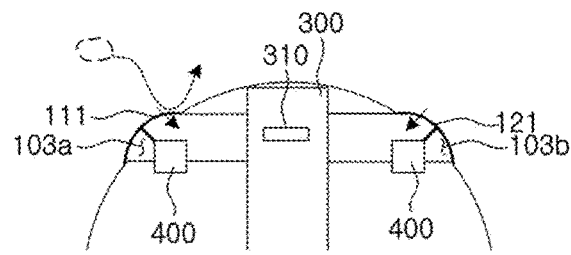
FIG. 4 is a diagram illustrating a state in which a suction device and a discharge device are closed.
Figure 5:
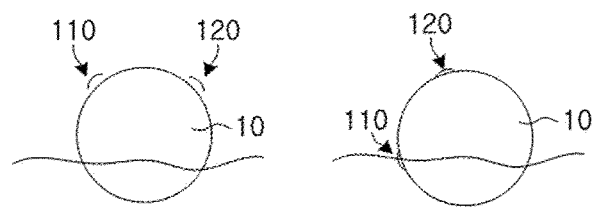
FIG. 5 is a schematic diagram illustrating a sensing operation according to a tilted angle of a floating-type contamination measurement apparatus.

FIG. 1 is a diagram illustrating a floating-type contamination measurement apparatus and an external monitoring device located on a closed space according to an embodiment of the present invention; FIG. 2 is a diagram illustrating the internal configuration of a floating-type contamination measurement apparatus; FIG. 3 is a diagram illustrating a state in which a suction device and a discharge device are opened; FIG. 4 is a diagram illustrating a state in which a suction device and a discharge device are closed; and FIG. 5 is a schematic diagram illustrating a sensing operation according to a tilted angle of a floating-type contamination measurement apparatus.

Referring to FIGS. 1 and 2, the floating-type contamination measurement apparatus 10 according to an embodiment of the present invention may be installed in a closed space 1.

Herein, the closed space refers to a place where workers can perform work, in which a risk of oxygen deficiency, a health hazard caused by harmful gases, fire or explosion due to flammable materials, etc. are present in a state of insufficient ventilation. Generally, these places may include wells, vertical shafts, tunnels, caissons, pits, culverts, manholes, tanks, reactors, septic tanks, settling tanks, sump tanks, etc., but the places are not limited thereto and any space may be applied as long as it is a space in which liquids are present, the ventilation is not sufficient and the water level therein is expected to fluctuate.

The floating-type contamination measurement apparatus 10 according to an embodiment may include a body part 100, buoyancy providing part 200, a measurement part 300, and an operation part 400.

The body part 100 may receive the buoyancy providing part 200, measurement part 300, and operation part 400, and may be disposed within the closed space 1. More specifically, the body part 100 may float on the liquids in the closed space 1 by buoyancy, and the height of the body part 100 from the bottom of the closed space 1 may vary in response to a change in the level of the liquids.

The body part 100 may include a first body part and a second body part (101, 102).

The first body part 101 may have a circular or square pillar shape, but the first body part 101 is not limited thereto.

The second body part 102 may be bound to the bottom surface at a lower end of the first body part 101 and can maintain the balance of the first body part 101 so that the body part 101 is maintained in a predetermined position. Additionally, the second body part 102 may have a hemispherical shape, and the planar region at an upper side thereof may be bound to the bottom face of the first body part 101 and the curved region at a lower side thereof may face with the liquids within the closed space 10. Additionally, the diameter of the upper surface of the second body part 102 may be formed to be larger than that of the rear surface of the first body part 101, and accordingly, the second body part 102 can support the first body part 101 from the lower side thereof and maintain the balance of the first body part 101, but the second body part 102 is not limited to have a hemispherical shape.

Additionally, the body part 100 may further include a third body part 103.

The third body part 103 may have a hemispherical shape. By having a hemispherical shape, the third body part 103 can allow the liquids, even when the liquids come into contact with the third body part 103, to rapidly flow down and thus can prevent the damage of the device.

Additionally, the third body part 103 may include the first body part and second body part (101, 102) inside thereof. The first body part 101 may be disposed such that it passes the center of the third body part 103. Additionally, the hemispherical shape of the second body part 101 may correspond to a partial region inside of the third body part 103. Accordingly, the curved region at a lower side of the second body part 101 can come into contact with a lower region at an internal side of the third body part 103.

Each of the first body part to the third body part (101, 102, 103) may be of a plastic material. Additionally, the third body part 103 may be of a glass material or a ceramic coating may be applied thereon so as to provide an anticorrosive property, but the material is not limited thereto.

The body part 100 may include a suction device 110 and a discharge device 120.

The suction device 110 and the discharge device 120 may be disposed on the third body part 103. Additionally, the suction device 110 and the discharge device 120 may be disposed on the upper end of the third body part 103. Additionally, when part of the lower end of the body part 100 is submerged, the suction device 110 and the discharge device 120 may be installed so as to correspond to the region of the body part 100 which is not submerged.

The buoyancy providing part 200 can allow the body part 100 to float on the liquids due to buoyancy. Additionally, the buoyancy providing part 200 may include a weight 210, and the weight 210 may be disposed at a lower side of the first body part 101 and may be disposed so as to correspond to the central region of the second body part 102 based on the second body part 102. That is, the buoyancy providing part 200 can be made to become a center region of gravity of the body part 100 so that the body part 100 can float in the liquids while maintaining a balance.

The lower region of the third body part 103 may be submerged in a liquid according to the weight of the weight 210. Additionally, from the positional view, all or part of the second body part 102 may be submerged into liquids, and additionally, even part of the lower end part of the first body part 101 may be submerged into liquids.

A measurement part 300 can measure the kind of material introduced from the outside and the concentration of the material whose kind is determined. In particular, the material introduced may be a material in a gaseous state.

The measurement part 300 may include a contamination level measurement sensor 310 and a processor 390.

The contamination level measurement sensor 310 is a sensor which can measure the kind of the material introduced into the body part 100 and the concentration of the material, and may include at least one selected from a non-dispersive infrared analyzer, a semiconductor-type gas sensor, a contact-fired gas sensor, an optical gas sensor, a temperature sensor, and a humidity sensor, but is not limited thereto, and any sensor which can determine the kind and concentration of the gas and can measure the temperature and humidity of the closed space 1 may be used.

The processor 390 can detect the level of air contamination due to harmful gases (e.g., carbonic acid gas, hydrogen sulfide, etc.) and oxygen concentration based on the sensing results of the contamination level measurement sensor 310.

In connection with the detection of harmful gases, harmful gases that cause the smothering action due to the poisoning of the body may be present in the closed space 1, in which ventilation is insufficient. These harmful gases are called chemical asphyxiants and their representative materials include carbon monoxide, hydrogen sulfide, methylene chloride, cyanide, etc. These harmful gases can cause a smothering action when exposed to the human body even under a normal oxygen concentration, and thus it is important to check the detection and concentrations of possible harmful gases that can be generated in a closed space 1 where it is highly likely that these harmful gases may be generated.

Additionally, in connection with the detection of oxygen concentration, in a case where the closed space 1 is an internal space of a steel tank, if there is water in the steel tank or the steel tank is sealed for a long period of time, the rust formed by oxidation of the internal wall can reduce the oxygen in the tank causing a state of oxygen deficiency, and may become a state of oxygen deficiency according to the rancidity of dry oil, respiration of microorganisms, and oxidation of stored products within the closed space 1. In this case, breathing air with an oxygen concentration of less than 16% will result in a lack of oxygen in the body tissue and acceleration of pulse and respiration rates thus showing symptoms such as vomiting and headache, whereas breathing air with the oxygen concentration of less than 16% will result in a loss of consciousness, seizure, decrease of blood pressure, and decrease in the number of pulsation, and thus the detection of oxygen concentration within the closed space 1 is important.

Further referring to FIGS. 3 and 4, an operation part 400 may operate a suction device 110 and a discharge device 120.

The operation part 400 may include a motor which is connected to a suction cover 111 of a suction device 110 and provides a power enabling the opening/closing of the suction cover 111 so that the suction cover 111 can move to an arrow direction, and may include a motor which is connected to a discharge cover 121 of a discharge device 120 and provides a power enabling the opening/closing of the discharge cover 121 so that the discharge cover 121 can move to an arrow direction.

The processor 390 can transmit a signal for controlling suction and discharge to the operation part 400 at a predetermined time point, and the operation part 400, and the operation part 400 can open/close the suction cover 111 and the discharge cover 121 in response to the signal for controlling suction and discharge. When the suction cover 111 is opened and thereby foreign materials are introduced into the body part 100, the contamination level measurement sensor 310 can sense the introduced materials, and the introduced materials can be discharged out of the body part 100 upon opening of the discharge cover 121.

Additionally, the body part 100 may further include a suction inlet 103a and a discharge outlet 140. A suction cover 111 may be bound to the suction inlet 103a and the suction inlet 103a may be opened or closed according to the horizontal movement of the suction cover 111, whereas a discharge cover 121 may be bound to the discharge outlet 103b and the discharge outlet 103b may be opened or closed according to the opening/closing movement of the discharge cover 121 to an arrow direction.

Additionally, to completely prevent the introduction of foreign materials into the suction inlet 103a and the discharge outlet 103b in a state where the suction inlet 103a and the discharge outlet 103b are closed, a rubber packing may be formed on each of the suction inlet 103a, discharge outlet 140, suction cover 111, and discharge cover 121, but is not limited thereto. Additionally, the suction inlet 103a and discharge outlet 103b and the suction cover 111 and discharge cover 121 may be coated with a material to which liquids cannot be attached.

The measurement part 300 may further include a position sensor 320.

The position sensor 320 may include at least one among a gyro sensor, an acceleration sensor, a gravity sensor, and a geomagnetic sensor, but is not limited thereto, and any sensor which can measure the position information of the body part 100, and more specifically, any sensor that can measure the height information of the body part 100 and the degree of inclination from the water surface may be used as the position sensor 320 of the present invention.

The processor 390 can transmit a signal for controlling suction and discharge to the operation part 400 when the angle of the body part 100 corresponds to that of the predetermined range based on the angle information of the body part 100 detected from the position sensor 320.

For example, referring to FIG. 5, when the floating-type contamination measurement apparatus 10 is inclined by the flow of the liquids, the sensing is stopped, whereas when the inclined angle corresponds to an angle within a predetermined range, foreign materials are sensed by opening the suction device 110, and then the introduced materials may be discharged by opening the discharge device 120. Accordingly, when the contamination measurement device 10 is inclined at an angle greater than a predetermined angle according to the flow of the liquids, it is possible to prevent the introduction of the liquids into the device by closing the suction inlet 103a and the discharge outlet 103b.

Additionally, when the inclined angle of the floating-type contamination measurement apparatus 10 is out of the predetermined angle range for a predetermined period of time, an abnormal signal can be transmitted to a monitoring device 20. When the floating-type contamination measurement apparatus 10 fails to establish a balance due to the structural characteristics of the closed space 1 or obstacles and the angle becomes out of the predetermined angle range and maintained as such for a predetermined period of time, the contamination measurement cannot be performed during such a period, and thus the abnormal state of position can be informed to an external monitoring device 20.

Meanwhile, although not shown in figures, the floating-type contamination measurement apparatus 10 may include at least one pan, and as a result, when the suction inlet 103a and the discharge outlet 103b are opened, the pan operates and facilitates easy introduction of air from the outside into the body part 100 and the discharge thereof.

The measurement part 300 may further include a communication part 330.

The communication part 330 can transmit/receive information by communicating with an external device or a secondary sensor or an alarm unit to be described later by wire or wireless communication.

In particular, the communication part 330 may be a device for performing wireless communication such as wire communication or infrared communication, communication using radio frequency, Bluetooth communication, etc. For example, it is preferred that wireless communication modes (e.g., Wireless LAN (WLAN), Wi-Fi, Wibro, Wimax, High Speed Downlink Packet Access (HSDPA), etc.) be used, but the wireless communication modes are not limited thereto, and wire communication modes (e.g., Universal Serial Bus, Ethernet, xDSL (ADSL, VDSL), Hybrid Fiber Coaxial (HFC) Cable, Fiber to The Curb (FTTC), Fiber To The Home (FTTH), etc.) may be used according to the system implementation modes. Additionally, near field communication technology (e.g., Bluetooth, Radio Frequency Identification (RFID), Infrared Data Association (IrDA), Ultra Wideband (UWB), ZigBee, Near Field Communication (NFC), etc.) may be used.

Meanwhile, the communication part 330 can transmit/receive information by communicating with the monitoring device 20.

In particular, describing the information on transmission/reception, when the monitoring device 20 transmits a sensing operation signal to the communication part 330, the processor 390 can operate the operation part 400 to detect the air quality within the closed space 1 and transmit the detection results to the monitoring device 20.

Additionally, when the monitoring device 20 transmits the position detection signal to the communication part 330, the processor 390 can transmit the detection results from the position sensor 320 to the monitoring device 20. Accordingly, the height of the floating-type contamination measurement apparatus 10 from the position sensor 320 can be detected, and accordingly, the water level of the liquids can be confirmed, and the abnormal position state of the floating-type contamination measurement apparatus 10 can be checked.

Meanwhile, the monitoring device 20 may be a terminal, and may include all kinds of handheld-based wireless communication devices such as Personal Communication System (PCS), Global System for Mobile communications (GSM), Personal Digital Cellular (PDC), Code Division Multiple Access (CDMA)-2000, W-Code Division Multiple Access (W-CDMA), Wireless Broadband Internet (Wibro) terminals, etc. Additionally, the monitoring device 20 may refer to a device capable of transmitting and receiving various data via a communication network according to a user's manipulation. Additionally, the monitoring device 20 may be provided with a memory for storing programs and protocols, a microprocessor for executing various programs for the purposes of calculation and control, etc. Additionally, the terminal 20 may include a Bus and at least one memory device connected to the Bus, at least one processor, a plurality of presentation devices, input/output ports, input/output devices, and a power supply. The memory device may include a hard disk, a volatile memory, a buffer, etc. Additionally, the processor can control the overall data communication of the monitoring device 20. Additionally, the presentation device may include a graphics card, a monitor device, and a display device. Additionally, the input/output ports can provide a connection for peripheral devices, such as digital cameras, printers, microphones, speakers, external storage devices, etc. Additionally, the input/output ports may be digital cameras, printers, speakers, external storage devices, etc. Additionally, a power supply may be provided so as to provide power to operate the monitoring device 20. Meanwhile, it is not necessary to provide all of the devices above so as to implement the monitoring device 20. Additionally, in an embodiment, when the monitoring device 20 is a portable computing device (e.g., a tablet PC, a smartphone, etc.), it may be integrated with a peripheral device (e.g., a digital camera, speaker, microphone, etc.). Additionally, the monitoring device 20 may include may include a bus, a display device connected to the Bus, an input/output unit, a processor, a memory unit, and a communication part.

The display device can display an image according to the liquid crystal display method, field emission display (FED) method, plasma display panel (PDP) method, electroluminescence (EL) device method, electrophoresis display method, and organic light emitting diode display method. The input/output unit may include a touch screen. Additionally, the input/output unit may include a touch screen and an input button, and additionally, the input/output unit may include a touch screen, an input button, and a camera unit. Additionally, the input/output unit may include a touch screen, an input button, a camera unit, and an acoustic system such as a microphone and a speaker. Meanwhile, the input/output unit is a term collectively referred to an input unit and an output unit, and the input unit may be a touch screen and an input button, and a camera unit and a microphone, and the output unit may be a vibrating device that generates vibration of a speaker and the monitoring device 20.

Figure 6A:
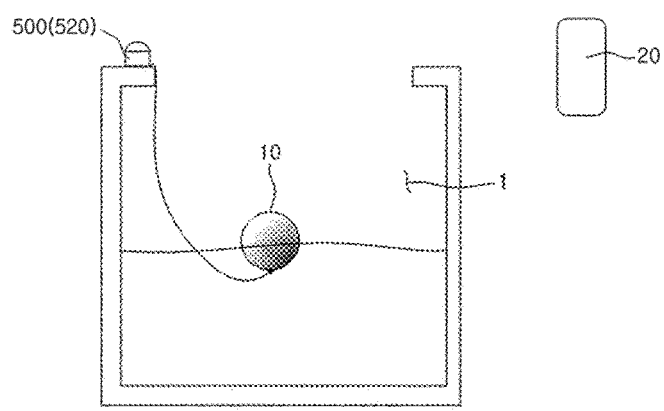
FIG. 6A is a schematic diagram illustrating a floating-type contamination measurement apparatus and an alarm unit, located outside the closed space, which is connected to the device by wire or wireless connection.

FIG. 6A is a schematic diagram illustrating a floating-type contamination measurement apparatus and an alarm unit, located outside the closed space, which is connected to the device by wire or wireless connection.

Further referring to FIG. 6A, the floating-type contamination measurement apparatus 10 according to an embodiment of the present invention may further include an alarm unit 500.

The alarm unit 500 may include a second alarm unit 520 located outside of the closed space 1.

The second alarm unit 520 may be connected to the floating-type contamination measurement apparatus 10 via a data transmission line and thereby receive signals from the floating-type contamination measurement apparatus 10. In particular, the data transmission line may penetrate through the second body part 102 to be inserted into the first body part 101 and thereby connected to the communication part 330.

Additionally, the second alarm unit 520 can perform an alarm operation in response to an alarm generation signal from the processor 390.

Additionally, the second alarm unit 520 may include at least one between a speaker for outputting an alarm as a sound and a light source for visually displaying an alarm.

Additionally, the power supply line tied together with the data transmission line may be connected between the second alarm unit 520 and the floating-type contamination measurement apparatus 10, and the second alarm unit 520 can deliver the power received from an external power supply source to the floating-type contamination measurement apparatus 10 via the power supply line. However, the method of power supply is not limited thereto but the floating-type contamination measurement apparatus 10 may be provided with a battery and utilize the self-power as a power source for operation.

Figure 6B:
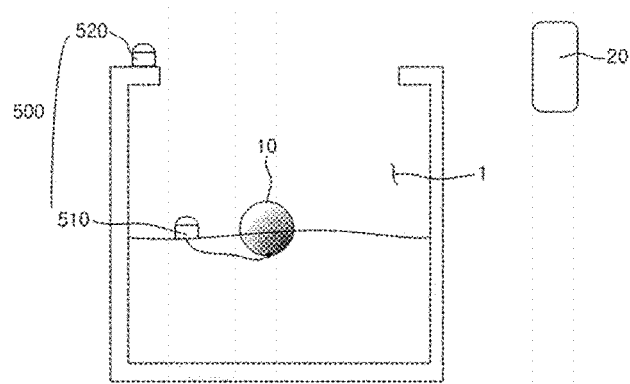
FIG. 6B is a schematic diagram illustrating a floating-type contamination measurement apparatus, and a first alarm unit located outside the closed space and a second alarm unit located inside the closed space, which are connected to the device by wire or wireless connection according to another embodiment.

FIG. 6B is a schematic diagram illustrating a floating-type contamination measurement apparatus, and a first alarm unit located outside the closed space and a second alarm unit located inside the closed space, which are connected to the device by wire or wireless connection according to another embodiment.

Further referring to FIG. 6B, the floating-type contamination measurement apparatus 10 according to an embodiment of the present invention may further include the alarm unit 500 in which a first alarm unit 510 and a second alarm unit 520 are provided.

The first alarm unit 510 may be installed on the body part 100 or may be formed in a separate configuration connected to the body part 100 by a wire. Additionally, when the first alarm unit 510 is a separate configuration connected to the body part 100 by a wire, it may be a floating type that can float in the liquids, such that the alarm can easily be identified from the outside, but the configuration is not limited thereto. Additionally, the first alarm unit 510 may include a mounting device that allows a worker within the closed space 1 to mount the first alarm unit 510 on the body part.

Additionally, the alarm unit 500 can perform an alarm operation in response to an alarm generation signal from a processor 390. Additionally, the second alarm unit 520 may be installed outside the closed space 1, in which case the second alarm unit 520 may perform an alarm operation in response to an alarm generation signal from the processor 390 via the communication part 330.

The alarm unit 500 may include at least one between a speaker for outputting an alarm as a sound and a light source for visually displaying an alarm.

Additionally, the processor 390 periodically operates the contamination level measurement sensor 310 so as to detect the contamination level according to the kinds and concentrations of harmful gases and oxygen concentration in the closed space 1, and in a case where a level of contamination not suitable for a worker to perform the work within the closed space 1 or an inappropriate oxygen concentration therein is detected, the processor 390 can transmit an alarm generation signal to the alarm unit 500 installed outside, and the alarm unit 500 can display an alarm in response thereto. Accordingly, the worker can check the status information of the closed space 1 via the alarm display of the alarm unit 500 before entering the closed space 1.

Additionally, the processor 390 can transmit the results of the contamination level measurement sensor 310 to the monitoring device 20. Accordingly, when the floating-type contamination measurement apparatus 10 is installed in each of a plurality of closed spaces, the monitoring device 20 can check and manage the overall contamination levels in the plurality of closed spaces.

Figure 7:
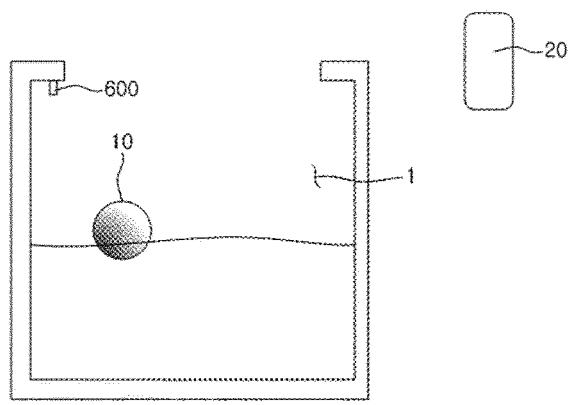
FIG. 7 is a schematic diagram illustrating a floating-type contamination measurement apparatus in a closed space and a secondary sensor.
Figure 8:
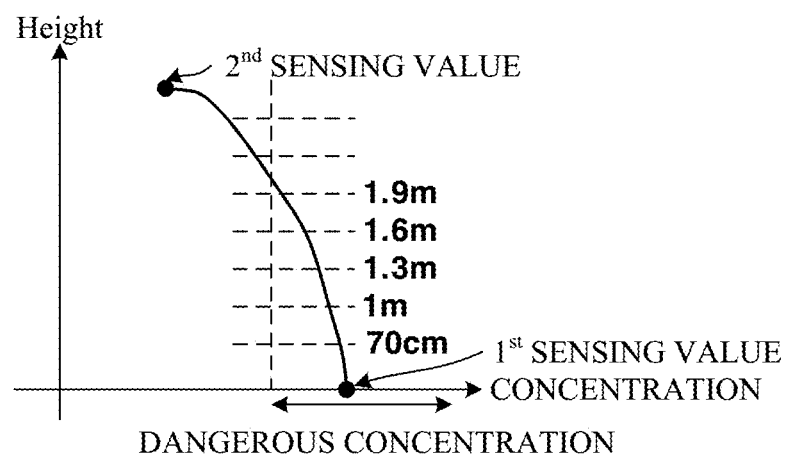
FIG. 8 is a graph illustrating the concentration of a harmful gas according to the height indicated in a monitoring device.

FIG. 7 is a schematic diagram illustrating a floating-type contamination measurement apparatus in a closed space and a secondary sensor, and FIG. 8 is a graph illustrating the concentration of a harmful gas according to the height indicated in a monitoring device.

Further referring to FIG. 7, the floating-type contamination measurement apparatus 10 according to an embodiment of the present invention may further include a secondary sensor 600.

The secondary sensor 600 may be fixedly installed in the upper end region of the closed space 1 and provide the sensing result to the communication part 330. Additionally, the secondary sensor 600 may be installed within the closed space 1 above the height where the body part 100 is located.

The secondary sensor 600 can measure the level of air pollution at the upper area of the closed space 1.

The processor 390 can calculate information on contamination according to height based on the detection result from the secondary sensor 600 and the detection result of the contamination level measurement sensor 310.

For example, when hydrogen sulfide which is mostly present in a lower layer of the closed space 1 due to specific gravity greater than air is present in the closed space 1, the concentration of the hydrogen sulfide detected from the contamination level measurement sensor 310 may be higher than the concentration of the hydrogen sulfide detected from the secondary sensor 600 and the concentration of hydrogen sulfide may become lower toward the higher end. In this case, the processor 390 can read the harmful gas concentration curve matching with the concentration of the hydrogen sulfide in the lower layer and the concentration of the hydrogen sulfide in the upper layer among the databases stored in the memory 340 and transmit it to the monitoring device 20. Additionally, the monitoring device 20, by indicating the harmful gas concentration curve and dangerous concentration according to height, can confirm in advance the possibility of occurrence of danger due to harmful gas according to the worker's working height, assuming that the worker has entered the closed space 1.

Furthermore, when the sensor is fixedly installed in a specific area of a closed space, the concentration may vary significantly depending on the kind of the harmful gas at a height other than the area where the sensor is located. In an embodiment, when the sensor is located at the top of the closed space and the specific gravity of the harmful gas is large, the height at which the worker's bronchi is located may vary depending on the working position and the worker's posture on a closed space 1, even when the worker judges from the detection result of the sensor that the concentration of the harmful gas in the closed space is at the normal level. Therefore, there is a possibility that the worker may inhale harmful gases at a dangerous level of concentration. Accordingly, it is possible to minimize the possibility of accidents by confirming the harmful gas concentration curve and the dangerous concentrations in advance.

Additionally, it is possible to check the concentrations of harmful gases according to height considering the characteristics of the harmful gases without attaching a sensor using the contamination level on the water surface from the floating-type contamination measurement apparatus 10 and the contamination level on the upper area from the secondary sensor 600, and thereby the installation cost can be reduced and the convenience of maintenance can be improved.

Additionally, when the secondary sensor 600 is installed in an area higher than the maximum water level considering the maximum water level of the liquids, it is possible to detect the danger according to height by interworking with the floating-type contamination measurement apparatus 10 while preventing the secondary sensor 600 from being damaged by liquids and blocking the problem of the sensor from being immersed into the liquids thereby preventing the occurrence of malfunctions and failures of the secondary sensor 600.

Figure 9:
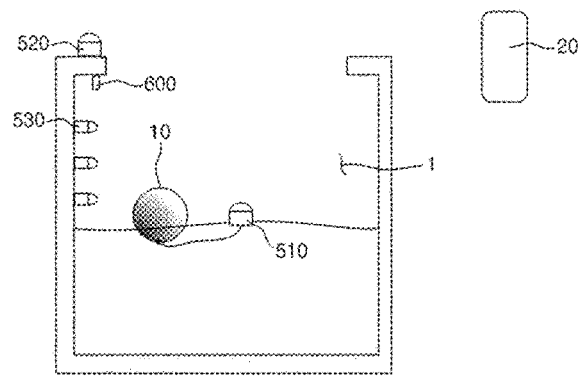
FIG. 9 is a schematic diagram illustrating a floating-type contamination measurement apparatus which is able to indicate the danger of the occurrence of an accident according to the height using a third alarm unit installed internal wall of a closed space.

FIG. 9 is a schematic diagram illustrating a floating-type contamination measurement apparatus which is able to indicate the danger of the occurrence of an accident according to the height using a third alarm unit installed internal wall of a closed space.

Referring to FIG. 9, the alarm unit 500 may include a third alarm unit 500.

The third alarm unit 530 may be provided in one or more than one, and may be installed in the inner wall in the closed space 1. When the third alarm unit 530 is provided more than one, they may be spaced apart from one another and installed on the inner wall in the closed space 1 at different heights from one another.

The processor 390 can calculate the information of contamination according to height based on the detection result from the secondary sensor 600 and the detection result of the contamination level measurement sensor 310, and transmit the information of contamination according to the corresponding height to each of the plurality of parts 530 installed according to height. Additionally, each of the plurality of parts 530 can visually and/or audibly display the level of contamination through the display of light emission and/or a sound based on the information of contamination received according to height. Accordingly, the worker can safely perform the work while checking the safe areas and unstable areas to perform the work by confirming the contamination level according to height of the closed space 1 through the display of alarm of the plurality of third alarm units 530.

Figure 10:
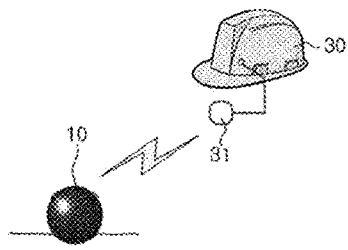
FIG. 10 is a diagram illustrating a floating-type contamination measurement apparatus which communicates with a safety display unit on a safety helmet.

FIG. 10 is a diagram illustrating a floating-type contamination measurement apparatus which communicates with a safety display unit on a safety helmet.

Referring to FIG. 10, the floating-type contamination measurement apparatus 10 can transmit the information of contamination detected from the closed space to a safety display unit 31 of safety helmet 30 which is worn by a worker, and the safety display unit 31 can display the light emission and a sound in response thereto. For example, in a case where the worker performs the work in a closed space with the safety helmet 30 on, the safety display unit 31 can display a green light indicating a safe state, and in a case of danger, an alarm sound can be outputted along with a red light. Accordingly, it is possible to improve safety of the working environment such that the worker can confirm the danger of the working environment via the safety display unit 31, which is installed on the safety helmet 30 and is thus located in the area where the worker can see in the field of view.

Additionally, a worker who works in a confined space with poor visibility due to poor external light will have a limitation on rapidly figuring out the changes in water level and will not be able to frequently check the changes in the concentrations of harmful gases according to the change in the water level in the area where the worker is located. However, according to an embodiment of the present invention, the worker can rapidly check the contamination level from the floating-type contamination measurement apparatus 10 in response to the changes in water level thereby capable of preventing safety accidents.

Figure 11:
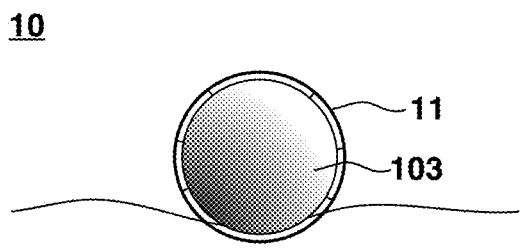
FIG. 11 is a diagram illustrating a floating-type contamination measurement apparatus which includes a ring section.

FIG. 11 is a diagram illustrating a floating-type contamination measurement apparatus which includes a ring section.

Referring to FIG. 11, the ring section 11 may be installed on the third body part 103 of the floating-type contamination measurement apparatus 10 according to an embodiment.

The ring section 10 may be formed around the third body part 103, and a particular space is formed between the ring section 11 and the third body part 103, and thus, the worker can easily pick up the device 10 by inserting forceps into the space between the ring section 11 and the third body part 103 when it is desired to pick up the device 10 floating on the closed space.

Figure 12:
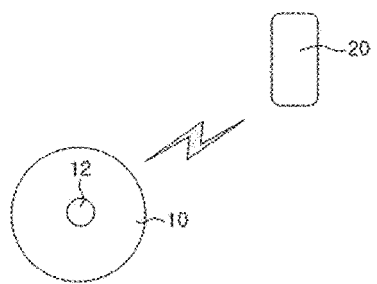
FIG. 12 is a diagram illustrating a floating-type contamination measurement apparatus which includes a light source unit.

FIG. 12 is a diagram illustrating a floating-type contamination measurement apparatus which includes a light source unit.

Referring to FIG. 11, the floating-type contamination measurement apparatus 10 according to an embodiment of the present invention may further include a light source unit 12.

The processor 390 can measure the receiving sensitivity of the communication part 330 according to the reception of at least one signal between a sensing operation signal being transmitted from the monitoring device 20 and a position detection signal, and when the receiving sensitivity measured is greater than the predetermined value, the light source unit 12 may be operated.

In other word, although the receiving sensitivity of the communication part 330 becomes deteriorated in the case of the closed space 1, when the entrance door of the closed space 1 opens, the receiving sensitivity of the communication part 330 can be increased, and the processor 390 detects the same and determines that the worker has opened the entrance door of the closed space 1 and thereby operates the light source unit 12. Additionally, the worker can easily locate the floating-type contamination measurement apparatus 10 according to the operation of the light source unit 12 and rapidly check the height of water level even in the closed space 1 where the field of view is poor in general due to the blocking of external light.

Although the present invention has been described with reference to preferred exemplary embodiments thereof, those skilled in the art or having knowledge in the art will appreciate that various modifications and substitutions are possible without departing from the concepts and technical areas of the present invention to be disclosed in the accompanying claims. Accordingly, the technical scope of the present invention should not be limited to the details described in the specification, but should be defined by the claims.

The present invention can be used in a technical field for detecting harmful gases, an oxygen concentration, etc. in a closed space so as to prevent safety accidents in advance.

Effects of the Invention

The embodiments according to the present invention can provides a floating-type contamination measurement apparatus which can measure the contamination concentration on the water surface irrespective of the level of the liquids in a closed space and detect the presence of harmful gases and oxygen deficiency in the closed space thus capable of preventing safety accidents.

Additionally, in an embodiment of the present invention, the information of the concentration of harmful gases according to height in the closed space can be provided using the sensing information of a secondary sensor thus capable of checking the danger according to the working position of the worker.

Additionally, in another embodiment of the present invention, the danger in a closed space can be provided in an audible and visual manner via an alarm unit installed outside the closed space.

Additionally, in still another embodiment of the present invention, it is possible to detect the level of contamination in a state where impurities are not introduced into the closed space by detecting the positional information of the device and performing the sensing operation based on the positional information.

What is claimed is:

1. A floating-type contamination measurement apparatus, comprising:

a body including a first body part having a circular or square pillar shape, a second body part having a hemisphere shape and a third body part having a spherical shape with a cavity, a suction inlet and a discharge outlet;

a suction device disposed in the suction inlet of the third body part; and a discharge device disposed in the discharge outlet of the third body party, wherein the first body part includes a buoyancy providing part which is received to the body and provides buoyancy to the body and a measurement part which is received to the body and measures the level of contamination in the cavity, the first body part is disposed perpendicular to a first flat surface of the second body part, the third body part is assembled into the first flat surface of the second body part such that the first body part is placed in the third body part, the suction device includes a suction cover and a first operation part connected to the suction cover, the discharge device includes a discharge cover and a second operation part connected to the discharge cover, the suction cover has a first curved shape and an edge portion of the suction cover is contacted with the third body part in the suction inlet when the suction device is closed, the discharge cover has a second curved shape and an edge portion of the discharge cover is contacted with the third body part in the discharge outlet when the discharge device is closed, the suction cover moves upward from a surface of the third body part when the suction device is open, the discharge cover moves upward from a surface of the third body part when the discharge device is open, the measurement part comprises a position sensor that detects the position of the body and a processor, and the processor detects the level of contamination in the cavity through a contamination measuring sensor disposed on the first body part based on the detection results from the position sensor, when the body corresponds to a predetermined position.

2. The floating-type contamination measurement apparatus of claim 1, wherein the measurement part detects a harmful gas in the cavity.

3. The floating-type contamination measurement apparatus of claim 1, wherein the measurement part detects the oxygen concentration in the cavity.

4. The floating-type contamination measurement apparatus of claim 1, wherein the suction device sucks the gas into the cavity and the discharge device discharges the sucked gas out of the cavity, and the measurement part measures the level of contamination in the cavity using the sucked gas.

5. The floating-type contamination measurement apparatus of claim 1, wherein the suction cover has a first curved surface and the discharge cover has a second curved surface.

6. The floating-type contamination measurement apparatus of claim 1, wherein the buoyancy providing part further comprises a weight located at a lower end region of the first body part.

7. The floating-type contamination measurement apparatus of claim 1, wherein the measurement part further comprises a communication part, and the processor transmits the measurement results to a monitoring device located outside of the cavity via the communication part.

8. The floating-type contamination measurement apparatus of claim 1, further comprising an alarm unit which performs the display of light emission and/or a sound based on the detection results of the measurement part.

9. The floating-type contamination measurement apparatus of claim 1, wherein the first body part is disposed in the cavity surrounded by the second body part and the third body part.

10. The floating-type contamination measurement apparatus of claim 1, wherein the suction cover is separated from the third body part when the suction device is open.

11. The floating-type contamination measurement apparatus of claim 1, wherein the discharge cover is separated from the third body part when the discharge device is open.

* * * * *